| United States Patent [19] | [11] Patent Number: 4,655,204 |
| Basuyaux | [45] Date of Patent: Apr. 7, 1987 |

[54] INTRAUTERINE CONTRACEPTIVE DEVICE FOR ANIMALS SUCH AS FEMALE DOGS

[75] Inventor: Michel Basuyaux, Lille, France

[73] Assignee: Societe Europeenne de Recherche d'Instrumentations Medicales Company, Paris, France

[21] Appl. No.: 612,900

[22] Filed: May 22, 1984

[51] Int. Cl.⁴ .............................................. A61F 5/46
[52] U.S. Cl. ................................................... 128/130
[58] Field of Search ................ 128/127, 128, 129, 130

[56] References Cited

U.S. PATENT DOCUMENTS

| 3,678,927 | 7/1972 | Soichet | 128/130 |
| 3,996,932 | 12/1976 | Csatary et al. | 128/130 |
| 4,353,363 | 10/1982 | Quesada | 128/130 |
| 4,449,980 | 5/1984 | Millar et al. | 128/130 |

Primary Examiner—Gene Mancene
Assistant Examiner—Cary E. Stone
Attorney, Agent, or Firm—Cushman, Darby & Cushman

[57] ABSTRACT

The disclosure embraces a contraceptive device of the type comprising a central stem and a device for maintaining in place the said stem at the interior of the uterine cavity of a subject, the device being composed of two elastic arms symmetrical in relation to the stem integral therewith at its tip; the arms naturally occupy a position in which they diverge beyond the tip by making an angle of value at least equal to that of the angle that is generally formed between each other of the two y-shaped channels of the uterus of females of a given animal species and more particularly the canine species so that the arms can be engaged in the y-shaped parts and can be maintained there by spreading effect produced by their natural elasticity.

4 Claims, 4 Drawing Figures

INTRAUTERINE CONTRACEPTIVE DEVICE FOR ANIMALS SUCH AS FEMALE DOGS

BACKGROUND AND SUMMARY OF THE INVENTION

Among the known methods of human contraception, is the one that consists in placing a contraceptive device inside the uterine cavity.

Many variations exist relating to the problem of maintaining the contraceptive device in place without causing any injury or embarrassment.

But the contraceptives known up to date are most often adapted to the uterus of a woman, the shape and dimensions of which are such that the device for maintaining in place the contraceptive is always supported on the intrauterine walls.

Up until now it has not been possible to utilize the known contraceptive principles used by women to apply them, by somewhat adapting them as need be, to animal species when it is desired to control birth only for those species having a uterus of the same type as that of a woman. For other species, this adaptation has been impossible, especially for canine and horse species.

In fact, the genital system of those species is quite different from that of a woman and no simple transposition has proven satisfactory.

That is the reason until now one had to be content with using less than effective methods such as the foams, oral hormonal contraceptives or injectable hormonal contraceptives, either radical, dangerous and burdensome such as ovariectomy (removal of ovaries) or tieing of uterine tubes.

It would be of the greatest interest for animal owners as well as for the animals themselves to be able to use a contraceptive because, as is known, it is a simple and not burdensome method, perfectly reversible (removal of the contraceptive is very easy in case of a wanted pregnancy), having no disadvantage concerning the health or behavior of the subject and, finally, being completely reliable.

To demonstrate the state of the art, one must note, especially, U.S. Pat. No. 3,507,274 which describes a contraceptive having divergent arms, the exterior faces 28 of which of the developed parts 24 must be in contact with the walls 29 of the interior 30 of the uterine cavity A, under the channels or openings D of the tubes (page 1, column 2, lines 55 to 59).

Also known is Great Britain Pat. No. A-2,079,158 relating to a contraceptive for females of certain animal species, but it contains no teaching relating to maintaining the contraceptive in place by the uterine prongs and, on the contrary, describes the placing of the contraceptive inside the uterine cavity itself, the whole contraceptive having sufficient elasticity to permit folding of its lobes (and not the arm) and their natural elastic unfolding (page 2, lines 31 to 37).

French patent No. A-78/16.160 also describes a contraceptive, the arms of which must be supported against the wall of the uterus as is specified page 1, line 17 and lines 19 to 22. The contraceptive according to the invention is intended for certain animal species and could not be used by women whose uterus is not provided with Y-shaped channels while the contraceptive described in this patent is usable only in medicine (and not in veterinary art), as the result of indications such as the words: "medicine" page 1, line 2, "comfort of the patient" page 1, line 10, "physician" page 2, line 27, etc.

Moreover, it is clearly established that this contraceptive does not have divergent arms beyond the top of the stem.

On the contrary, the present invention permits the making of a contraceptive intended for females of animal species whose uterine cavity is different from that of the human species, and this is the case, more particularly, of bitches.

A contraceptive according to the invention is of the type comprising a central stem and a device for maintaining in place the said stem at the interior of the uterine cavity of a subject, said device being composed of two elastic arms which are symmetrical in relation to the stem integrally therewith at its top, and which naturally occupy a position in which they diverge beyond the top of the stem by making an angle between each other, characterized in that the top of the stem must be located in the neighborhood of the bottom of the uterine cavity, the arms must be placed beyond this cavity, in two uterine Y-shaped channels which the uterus of females of a given animal species has, and more particularly the canine species, the angle of the arms being greater than that which the said uterine Y-shaped channels make between each other.

According to other characteristics of the invention:

the arms bear on their extremity exterior outlines having a nonwounding bent surface and, preferably, giving to the extremity of each arm a half-ovoid shape;

the contraceptive in fact is a synthetic material, such as polyethylene, containing particles of dispersed copper;

the contraceptive is made of a synthetic material, such as polyethylene, containing at least a metallic salt such as barium sulfate.

The invention will be better understood by the following detailed description made by referring to the attached drawing. Of course, the description and the drawing are given only as an example and not as limitation.

DETAILED DESCRIPTION OF THE INVENTION

Figure 1:
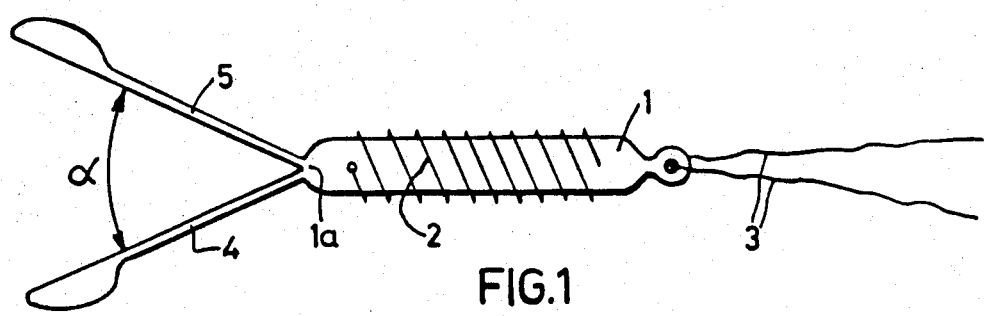
FIG. 1 is a schematic profile view of a contraceptive according to the invention.

By referring to FIG. 1, a contraceptive according to the invention is seen of the type comprising a central stem 1 on which is wound, as is known, a copper wire 2 and which is provided at its base with a transversal passage for two strings 3 intended to locate and extract the contraceptive as is well known with the contraceptives intended for women.

The top 1a of the stem 1 is integral of two arms 4 and 5, the assembly of the stem 1 and the two arms 4 and 5 being advantageously obtained by molding in a sole piece of synthetic material, in order that those two arms 4 and 5 be elastically deformable while having sufficient firmness and "memory".

In fact, the arms 4 and 5 must naturally occupy a position in which they diverge, beyond the top 1a, by making between each other an angle α.

The arms 4 and 5 are capable of being folded one towards the other, against their elasticity, so that they are placed in the extension of the stem 1. So that they fit well one against the other, they face each other by a plane surface.

Figure 2:
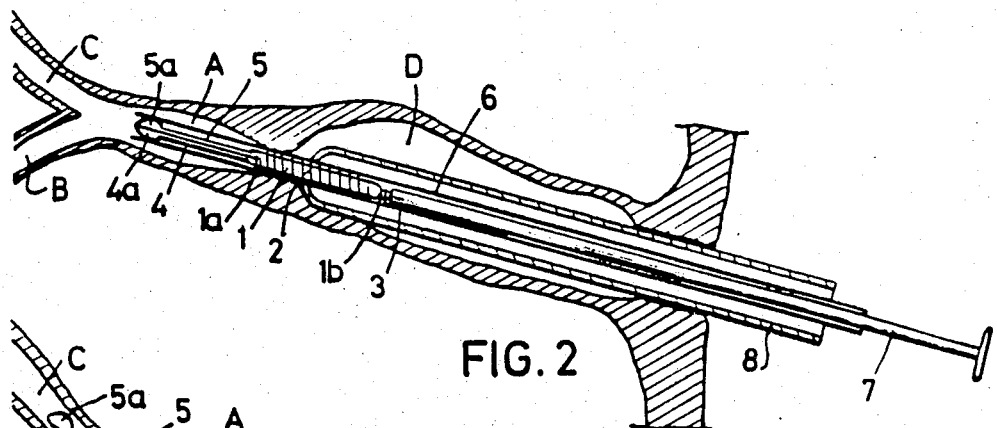
FIGS. 2, 3 and 4 are schematic views showing the placing of a contraceptive according to the invention in the uterine cavity of a bitch.
Figure 3:
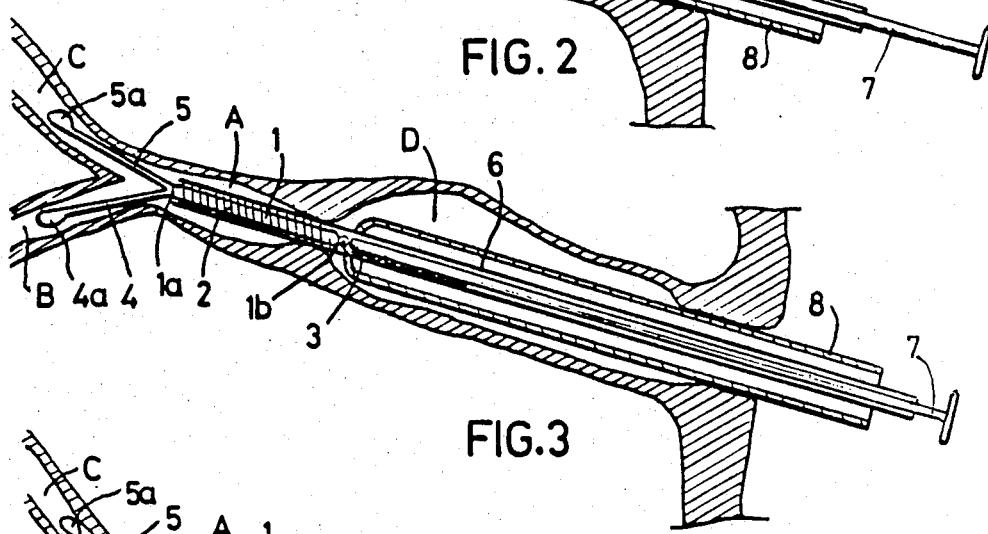

In this way, they can both be engaged with the stem 1 in a detachable tube of a small diameter 6 as is shown on FIGS. 2 and 3.

The contraceptive which has just been described is of the intra-uterine type, that is, it must be placed entirely at the interior of the uterine cavity of the subject, the top 1a being located at the bottom of this cavity A.

It is intended for females of an animal species whose uterus A has two Y-shaped channels B and C.

The latter diverge by forming a virtual angle, the value of which is sufficiently well known that it will be sufficient to give a good approximation, at least for a given race.

The angle α is chosen to be at least equal to this natural angle of the uterine channels in order that the arms 4 and 5 can be engaged each in one of the two Y-shaped channels B and C, that is, beyond the uterine cavity A per se.

They are maintained there by the effect of spreading apart that their natural elasticity produces from the fact that they could not be extracted accidentally and thus cause expulsion of the stem 1 only if they were brought nearer together according to an angle about equal to that of the channels B and C.

Figure 4:
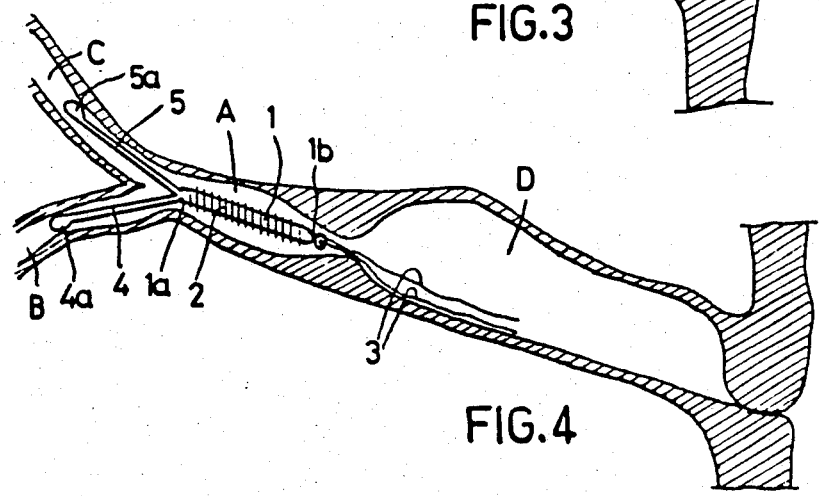

Referring now to FIGS. 2 to 4, the placing of a contraceptive according to that of FIG. 1 will be described.

The arms 4 and 5 are brought down one against the other and the assembly of the stem 1, the strings 3 and the arms 4 and 5 are engaged in the tube 6.

On the other extremity of the tube 6, a pusher 7 is engaged and the whole is engaged in a cannula 8 of the human rectoscope type of desired dimensions.

The cannula 8 is engaged in the vulva and is pushed until its extremity hits in the bottom of vagina D at the entrance of the uterus A, that is in relation to the external opening of the neck of this uterus A.

Then the tube 6 is pushed so it passes the neck and spreads at the interior of the uterus A, which is shown on FIG. 2.

Then the pusher 7 is pushed while retaining or by pushing the tube 6 so that the arms 4 and 5 of the contraceptive escape from this tube 6 which, no longer gripping them, lets the natural elasticity of the material which forms them act to cause their spreading apart.

By pushing the body 1, one assures that it is quite entirely placed in the uterine cavity A, the top 1a must then be in the neighborhood of the bottom of the cavity A, which corresponds to the correct placing of arms 4 and 5 because, of course, the relative dimensions of the body 1 and the arms 4 and 5 are fixed according to the subject, that is in relation to the estimated depth for a given breed. Thus, one can, for example, dispose of three contraceptive formats corresponding, respectively, to bitches of "small", "medium" and "large" breeds.

FIG. 3 shows an intermediate phase of the setting in place which corresponds to the beginning of penetration of the arms 4 and 5 in the channels B and C, the stem 1 of the contraceptive still not being pushed sufficiently so that its top 1a is located at the bottom of uterine cavity A.

When that is obtained, as specified above, the tube 6, pusher 7 and the cannula 8 are withdrawn simultaneously. The contraceptive is now fixed in place as is shown on FIG. 4.

It is seen, on this FIG. 4, that the contraceptive is placed much higher in the uterus that the known contraceptives, in order that its top 1a be located at the outlet of the channels B and C, where its contraceptive action is already taking place.

The base 1b of the stem 1 is formed like those of the devices used by women, that is, it has a nonwounding shape favorable to tieing the threads 3 by which one can proceed to extract the contraceptive, as is known per se.

In order to facilitate the setting in place of the contraceptive device, that is , the successful introduction of arms 4 and 5 in the Y-shaped channels B and C, the extremity of those arms 4 and 5 is provided respectively with exterior contours 4a and 5a having a nonwounding curved surface.

Those reliefs form superthicknesses which in a way play the role of skates, effortlessly sliding against the walls of the Y-shaped channels B and C and thus opposing any perforation caused by the extremity of arms 4 and 5.

In order to make sure that those reliefs play their role whatever happens to be the precise morphology of a given subject, it is good that those reliefs 4a and 5a have a profile corresponding to a surface of revolution but as it is also important that the arms 4 and 5 can be placed one against the other in the tube 6 of the smallest possible diameter, it is good that the volume resulting from this surface of revolution come from the combination of the two reliefs 4a and 5a. Each must then have the form of a hemiovoid or analogous (hemisphere, etc.).

The stem 1 and the arms 4 and 5 are advantageously molded of synthetic material such as polyethylene and the copper wire 2 is wound around the stem 1 as is known per se.

But there can also be mixed with the polyethylene, before molding, copper particles which will be suitably dispersed as well as, in case of need, particles of a metallic salt such as barium sulfate.

This will reinforce the contraceptive power by an ionization process not only towards the walls of the uterine cavity A, but also towards the walls of the Y-shaped channels B and C, thanks to the position that the contraceptive device occupies according to the invention and thus thanks to its particular structure.

I claim:

1. A contraceptive device for female animals of the canine specie comprising a central stem member having a first end and a second end spaced from said first end, said stem having means at said first end for securing means for retrieving said contraceptive device from the womb of a animal, and means at said second end for maintaining said contraceptive device in place in the womb of the animal, said means at said second end including a pair of diverging substantially straight arms having a selected angle therebetween with each arm terminating in smoothly curving surfaces, said angle between said arms being greater than the angle formed between the y-shaped channels of the uterus of said animal.

2. Contraceptive device according to claim 1, characterized in that it is made of a synthetic material, such as polyethylene, containing particles of dispersed copper.

3. Contraceptive device according to claim 1, characterized in that it is made of a synthetic material, such as polyethylene, containing at least a metallic salt such as barium sulfate.

4. The contraceptive device as claimed in claim 1 wherein said curved surfaces of the ends of said arms are hemi-ovoid in shape.

* * * * *